United States Patent [19]

Fuchs, deceased et al.

[11] 4,291,698
[45] Sep. 29, 1981

[54] BUTTON FOR SURGICAL APPLICATIONS

[75] Inventors: Heinz Fuchs, deceased, late of Melsungen, Fed. Rep. of Germany, by Hedwig Fuchs, heir; Hans-Friedrich Müller, Hamburg; Hildegard Hecht, Spangenberg, both of Fed. Rep. of Germany

[73] Assignee: Intermedicat GmbH, Emmenbrucke, Switzerland

[21] Appl. No.: 98,184

[22] Filed: Nov. 28, 1979

[30] Foreign Application Priority Data

Dec. 9, 1978 [DE] Fed. Rep. of Germany ....... 2853289

[51] Int. Cl.³ ............................................... A61B 17/04
[52] U.S. Cl. ............................... 128/335; 24/132 AA; 24/255 SL; 128/346
[58] Field of Search ........... 128/346, 325, 335, 334 R, 128/326, 335.5; 251/10; 43/44.91; 24/132 R, 132 AA, 132 WL, 255 SL, 255 R, 129 R, 129 D, 120, 121; 112/253

[56] References Cited

U.S. PATENT DOCUMENTS

| 2,087,420 | 7/1937 | Wiederholt | 24/132 R X |
| 3,461,876 | 8/1969 | Miller | 128/346 |
| 3,976,079 | 8/1976 | Samuels et al. | 128/335 |
| 4,145,833 | 3/1979 | Ratte | 43/44.91 X |
| 4,183,120 | 1/1980 | Thorne | 24/255 SL X |

FOREIGN PATENT DOCUMENTS 569957 6/1945 United Kingdom ............ 24/132 R

Primary Examiner—Michael H. Thaler
Attorney, Agent, or Firm—Merriam, Marshall & Bicknell

[57] ABSTRACT

A button for surgical applications comprising a disk having a slot which extends to a passage for guiding a thread therethrough within the circumference of the disk, said passage being sealed by a clamping device for clamping the thread firmly in the passage. The clamping device includes a disk segment movable parallel with the disk over the slot and passage to a latched position where its inner marginal part is past the passage thereby bending the thread and holding it by friction and compression.

10 Claims, 6 Drawing Figures

BUTTON FOR SURGICAL APPLICATIONS

This invention relates to a button for surgical applications, comprising a disk having a slot which extends to a passage for guiding a thread therethrough within the circumference of the disk, said passage being sealed by a clamping means for clamping the thread firmly in the passage.

In the surgical closing of wounds it frequently is necessary to anchor suture material threads, which are placed under a more or less strong tensile stress, on the skin. The anchoring means must be able to remain up to several weeks on the site without damage to the skin, and it is supposed to accommodate the traction forces which act in differential and alternating force on these threads, so that a relief from stress of the wound area is brought about. Freedom from stress of the tissue at the wound suture is an important prerequisite for the satisfactory healing of tissue because stress or tension of the tissue along the sealing line of a wound involves a continuing danger that the wound would again break open mechanically. Moreover, tension interferes with the healing process itself.

A simple button suture frequently is unable to provide the necessary freedom from tension on the tissue because, due to the small contact surface of the thread on the skin, it would induce the risk of a pressure necrosis. To enlarge the contact surface, and thus to relieve the skin, bulge sutures, plates or buttons are used. With bulge sutures the thread must be slung around bulges and be knotted. This is complicated. In the case of the known plates and buttons, it is necessary in each case, in addition to the knotting, that the thread must be threaded through axial passages, which is a complicated method from a technical point of view for the surgeon, and also time-consuming. When securing a thread, threaded through a button by means of lead spheres, there is the additional disadvantage that an anchoring of the thread is not assured. While it is possible, but only with difficulty, to pre-apply the correct tension to the thread as a result of the threading and knotting, the thread will loosen and eventually would have to be re-tensioned. However, re-tensioning is practically impossible with a knotted thread.

A button which eliminates knotting of the thread, by a clamping part which secures the thread at the button, is described in U.S. Pat. No. 2,075,508. That button has a slotted disk or a strip riveted on a plate-shaped disk. The rivet is axially perforated so that a thread can be conducted through the button, said thread being firmly clampable between the plate-shaped disk and the clamping part. This button, too, has the disadvantage that the thread must be threaded into the head in a complicated manner. Moreover, both the application of the proper thread tension, and readjustment of the thread tension, are problematical.

Use of a button disclosed in the German published patent application No. 2,157,529 involves substantially the same problems. That button has a radial hole, intersecting the axial disk hole, for guiding the thread. A pin, insertable into said radial hole, firmly clamps the thread, guided through the axial hole, between the pin itself and the wall of the hole. It has been demonstrated that the handling of this button, too, is complicated and requires great skill on the part of the surgeon because the thread again must be threaded into a hole. Securing of the thread with the pin is not dependable and correction of the thread tension is impossible because it is no longer possible to seize the pin and pull it out of the radial hole.

One possible way to facilitate the insertion of the thread into the axial passage of the disk and to clamp it in the passage is described in the U.S. Pat. No. 3,976,079. There a slot is formed connecting the central axial passage for the thread with the circumference of the disk, so that the thread can be introduced from the disk periphery radially into the passage and axial threading is eliminated. A ratchet with a serrated part, pivotable about a shaft transversely to the plane of the disk, as shown in FIG. 13 of the patent, is used as a clamping means and it presses the thread against an inner wall of the disk. The inner wall extends straight and axially to the passage. The firmly clamped thread extends rectilinearly and is free from reversal in the area of the clamping zone through the disk, so that it is clamped only over a short length of thread. Nevertheless, to assure safety against shifting of the thread, serration of the ratchet is necessary. However, this is undesirable because with the ratchet closed, the teeth could damage or even sever the thread, causing loss or reduction of the breaking strength or, in case of severance, failure of the fastening as such. Moreover, it is disadvantageous that the clamping means is not securable, so that unintentional loosening of the thread becomes possible. This danger is enhanced by the fact that a planar and narrow handle part of the ratchet protrudes over the disk plane so that an object sliding over the button can firmly hook the handle and release the ratchet. Also, even with the ratchet closed, the radial slot of the disk remains open. As a result, surgical dressing material can hook into the disk slot making problematic the firm placement and safety of the thread.

The invention is based on solving the problem of so designing a button of the above mentioned kind so as to secure the sutures and to relax the tissues at the wound suture so that a higher tensile strength, and particular assurance against sliding of the thread, will be attained and that a reliable permanent action of the clamping means is assured, even under unfavorable external conditions without requiring therefor any particular skill and attention on the part of the surgeon.

This problem is solved, according to the invention, by a clamping means consisting of a disk segment which is movable parallel with the disk over the slot into a latching terminal or closed position, so that the inner marginal part is positioned behind or past the thread passage.

In such a two-part button, the thread is bent angularly in the terminal or closed position of the button, and securely clamped between the disk and disk segment against sliding. The angular bending of the thread results in it being clamped over a relatively long length, thereby producing a higher tensile strength grip on the thread and, especially, safety against sliding.

To place the button at a wound suture, the thread is introduced into the slot in the disk and the disk segment is moved by lateral pressure parallel with and into position on the disk, whereby the disk segment inner marginal part pushes the thread along and through the slot into the thread passage, desirably axially located, in the disk. When additional pressure is exerted against the disk segment it moves into a latching position with its inner marginal part pressing the thread behind the passage, and clamping it firmly in an angled position, resulting in its being safely secured without, however, thereby shearing or damaging the thread. By latching the disk segment in the terminal or closed position, the disk segment always and positively occupies its closed position with maximum clamping effect on the thread, without the surgeon having to pay further attention to it. Moreover, the latching means prevents unintended loosening of the disk segment thread clamping means from clamping engagement with the disk.

In using the button, either the thread to be secured can be pulled laterally toward it and through the open slot into the thread passage, or the disk can be pushed from the side onto the thread. An opened button always has the slot and passage freely accessible, and the surgeon is able to handle the button in different ways in accordance with actual conditions. The thread can be inserted into the passage with one hand.

Advantageously, the disk is connected to the disk segment via a flexible hinge, so that the button can be handled as a unit. As the surgeon applies the button, he is able to easily and effortlessly control the thread tension with his one hand and to place the button in the desired position with his other hand and to then firmly clamp it to the thread. The handling of the disk and of the clamping means is extraordinarily simple and uncomplicated and the dependable clamping of the thread assures freedom from tension on the tissue at the wound suture, which is indispensable for problem-free healing of tissue.

In a particularly advantageous embodiment of the invention, the disk is a parallel-sided housing, with the thread passage and the slot being located in one wall of the housing wall, while the housing other wall is smaller than the first wall and is recessed past the passage. The disk segment inner marginal part or edge extends into a recess in the housing and nests, in closed position, in the recess in the housing. This construction offers the advantage in that, in its movement relative to the disk, the disk segment is guided so as to be free of any rotation in the housing, and that upon penetration of the disk segment into the housing recess, the thread is bent repeatedly and clamped on both sides of the disk segment between a disk segment surface and a housing wall. This produces an outstanding slide-safe clamping of the thread in the button. An additional clamping effect is exerted on the thread between the recessed edge of the recessed housing wall, and the inner marginal part of the disk segment. If this additional clamping effect is not desired, the edge of the recessed housing wall may be provided with a recess or clearance space in alignment with the thread passage, through which the thread can pass without being clamped between the inner marginal part or edge of the disk segment and the recessed edge of the recessed housing wall.

The inner marginal part or edge of the disk segment may be straight and smooth or serrated. The teeth of a serrated edge prevent the thread from sliding laterally during clamping. Alternately, the inner marginal part of the disk segment may be arcuate, such as semi-circular. With this design, the path of the bent thread within the housing cavity of the disk becomes particularly long and the friction exerted on the thread is increased.

To secure the disk and the disk segment in the closed position, a click-stop latch is desirably used. It is formed advantageously from hooks which grip together. One hook can be provided on a flexible arm and have a nose protruding over the outer circumference of the disk. The nose protruding beyond the outer circumference of the disk permits a simple unlatching of the click-stop latching device to release clamping of the thread. In that way, a correction of the thread tension by increased or decreasing thread tension is possible at all times. An outwardly protruding finger likewise is desirably appropriately placed on the disk segment in the proximity of its hook. With the click-stop latch closed, the nose and finger are so oriented in relation to each other that compression on them between the thumb and index finger causes a release of the latched hooks, the thread clamping slot is exposed and the grip on the thread is released. The button can be opened or closed with one hand. The other hand is free to manipulate the thread.

Upon engagement or closing of the click-stop latch, the outer contours of the disk and the disk segment advantageously supplement each other to form a symmetrical button. The button may have any rounded shape. It preferably is shaped like a circular disk. The button can be manufactured in different sizes, depending on the strength of the thread and the tensile stress to be expected. A button with flat, smooth contours assures good compatability with the skin surface and to a surgical dressing, because it will not have an abrasive action on the surgical dressing. The button is universally applicable for all supporting sutures as, for example, sutures located on the abdominal cover (ventrofile), in plastics, in tendon sutures, intracutaneous sutures, etc.

The button desirably is made completely of a solid polymeric material which provides irritation-free, good compatibility with the skin. If necessary, the button can be provided with a foam rubber cushion having an outer textile fabric cover.

The invention will be described further in conjunction with the attached drawings, in which.

Figure 1:
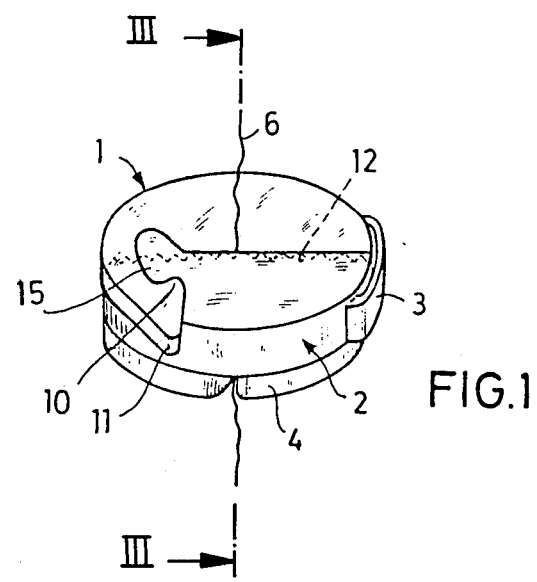
FIG. 1 is an isometric view of a closed button according to the invention.

The button for securing surgical suture material is designed as a circular disk with smooth surfaces consisting essentially of a disk 1 and a disk segment 2, which are interconnected by means of a flexible hinge 3. Both the disk 1 as well as the disk segment 2 and the flexible hinge 3 are appropriately manufactured from synthetic polymeric material.

The disk 1 is designed as a parallel-sided housing, whose one wall 4 is provided with a slot 7, which has a closed end forming a passage 5 for a thread 6. The other wall 8 is recessed beyond the passage 5. Wall 8 carries an arm 9, at the end of which is located an inwardly oriented hook 10. Hook 10 has a nose 11 protruding beyond the outer circumference or edge of the disk 1.

The disk segment 2 has an inner marginal part 12 extending into the cavity 13 of the housing, and in the closed condition of the button it is located past the thread passage 5 in the wall 4 of the housing of the disk 1. The essentially straight edge 12 may be serrated to prevent lateral shifting of the thread during closing of the button. In the closed position of the button, the recess edge 14 of the disk segment 2 butts against, or is very close to, the edge of the wall 8 of the disk, and an outwardly directed hook 15 on the disk segment grips behind the hook 10 of the disk 1 as a click-stop latch. To release the click-stop latching between both hooks 10 and 15, pressure is applied against the nose 11 of the hook 10, whereupon the disk segment 2 is released from the grip with the disk 1 (FIG. 2).

Figure 3:
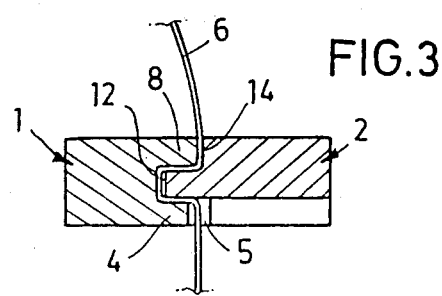
FIG. 3 shows a cross-section taken along the line III—III of the closed button according to FIG. 1.

The disk 1 and the disk segment 2 co-act like clamping jaws, between which the thread 6 is bent and firmly clamped. The thread 6 is introduced into the disk 1 of the open button from the side through the slot 7 into the passage 5. Then the thread 6 is secured by lateral contact pressure against the disk segment 2 which moves the inner edge 12 into the housing cavity 13. In the latched or closed condition of the button, the thread is bent several times and clamped several times between co-acting clamping surfaces, as illustrated in FIG. 3. Thread sliding, as a result, is practically impossible.

Figure 2:
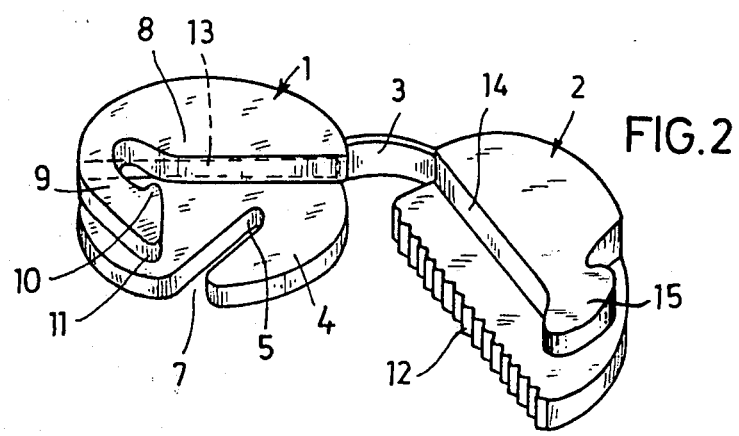
FIG. 2 is an isometric view of the button of FIG. 1 opened.

The second button embodiment corresponds functionally and substantially with the button shown in FIGS. 1 to 3; however, its construction is slightly modified.

The disk 20 is provided at its wall 21 with an outwardly rounded and flared slot 22 which terminates in a sharply bent passage 23 for a thread 6. The passage 23 is substantially in alignment with a recess 24 in the other wall 25 of the disk 20. A slightly bent arm 26 of the wall 25 carries an inwardly oriented hook 27, and an outwardly protruding nose 28.

Figure 4:
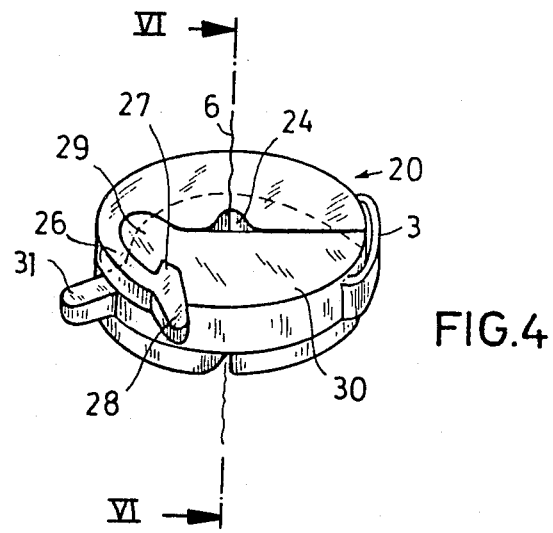
FIG. 4 shows an isometric view of a second embodiment of a closed button according to the invention.
Figure 5:
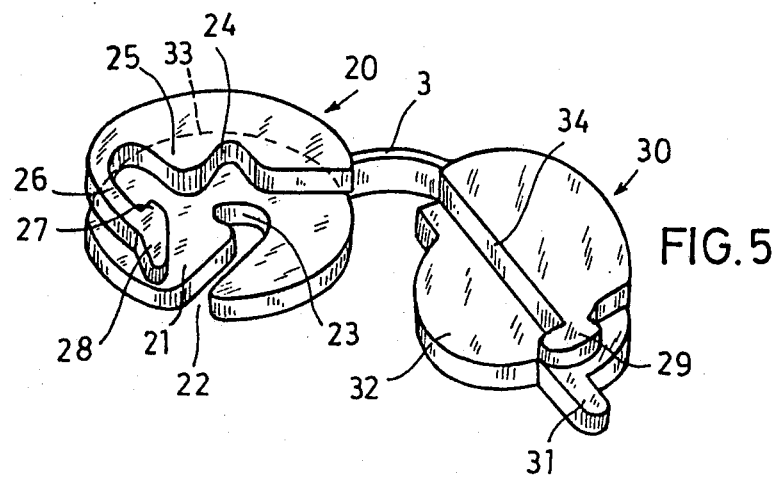
FIG. 5 shows an isometric view of the button shown in FIG. 4 in open position.
Figure 6:
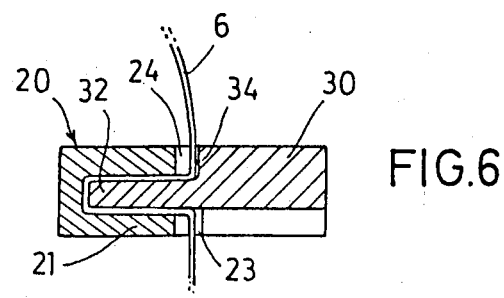
FIG. 6 shows a cross-section taken along the line VI—VI of the closed button shown in FIG. 4.

An outwardly oriented hook 29 on disk segment 30 grips or latches together with the hook 27. An outwardly directed finger 31 also is associated with, but beneath, the hook 29, which in latched condition of the button is located behind the nose 28 in the direction of the closing movement of the disk segment 30 (FIG. 4). The result is that both hooks 27 and 29 are released from latching engagement from each other by compressing the nose 28 and finger 31 between thumb and index finger, so that the button can be opened with one hand.

The inner part 32 of the disk segment 30 in this embodiment is semi-circularly arcuate. The cavity 33 of the disk 20 is of similar design so that inner marginal part 32 can nest in cavity 33.

The arcuate inner marginal part 32 may be smooth-edged, because lateral sliding of the thread is prevented by the recess 24 in the wall 25 of the disk 20.

When the button is being closed, thread 6 is pushed by the semi-circular arcuate inner marginal part 32 of the disk segment 30 far into the cavity 33 in the disk 20. Because of the large thread loop so formed, the length of the thread portion clamped between the housing walls 21 and 25 and the disk segment part 32 is larger than in the embodiment of FIGS. 1 to 3. The larger clamped-in thread length provides a slide-safe hold of the button on the thread, although the edge of the recessed wall 25 in the area of the thread passage is recessed, and does not adhere at this point against the recessed edge 34 of the disk segment 30, so that no additional clamping effect is applied to the thread at this point.

The foregoing detailed description has been given for clearness of understanding only, and no unnecessary limitations should be understood therefrom, as modifications will be obvious to those skilled in the art.

What is claimed is:

1. A button for surgical applications comprising a disk having a parallel-walled housing, a slot which extends to a thread passage for guiding a thread therethrough within the circumference of the disk, the thread passage and the slot being in one housing wall, the other housing wall being recessed past the passage, said passage being closeable by a clamping means for clamping the thread firmly in the passage, with the clamping means including a disk segment rotatably joined to and movable parallel with the disk over the slot and thread passage to a latched position where its inner marginal part is past the thread passage, and in the latched position the disk segment inner marginal part protrudes into a cavity past an edge of the disk recessed housing wall and a disk segment recessed edge behind the inner marginal part is adjacent said edge of the disk recessed housing wall.

2. A button according to claim 1 in which the edge of the recessed housing wall has a recess aligned with the thread passage.

3. A button according to claim 1 in which the inner marginal part of the disk segment is of rectilinear shape.

4. A button according to claim 1 in which the inner marginal part of the disk segment is semi-circularly arcuate.

5. A button according to claim 1 in which the disk is connected to the disk segment via a flexible hinge.

6. A button for surgical applications comprising a disk having a parallel-walled housing, a slot which extends to a passage for guiding a thread therethrough within the circumference of the disk, the thread passage and the slot being in one housing wall, the other housing wall being recessed past the passage, said passage being closeable by a clamping means for clamping the thread firmly in the passage, with the clamping means including a disk segment rotatably joined to and movable parallel with the disk over the slot and thread passage to a latched position where its inner marginal part is past the thread passage, and in the latched position the disk segment inner marginal part protrudes into a cavity past an edge of the disk recessed housing wall and a disk segment recessed edge behind the inner marginal part is adjacent said edge of the disk recessed housing wall, and with the disk and disk segment including a click-stop latch for releasably latching them together in said latched position.

7. A button according to claim 6 in which the click-stop latch comprises two hooks gripping with each other with one hook being on the disk and the other hook on the disk segment, and with one hook having a flexible arm with a nose protruding over the outer circumference of the disk.

8. A button according to claim 7 in which the second hook has an outwardly protruding finger.

9. A button according to claim 8 in which, when the latch is locked the two hooks engage each other between the nose and the finger so that when the nose and finger are pressed towards each other the hooks disengage and the latch is opened.

10. A button according to claim 6 in which with latching engagement of the click-stop device the outer contours of the disk and of the disk segment form a symmetrical body.

* * * * *